US00PP17238P3

(12) United States Plant Patent
Sanders

(10) Patent No.: US PP17,238 P3
(45) Date of Patent: Nov. 28, 2006

(54) ***IMPATIENS* PLANT NAMED 'IMTRAROSE'**

(50) Latin Name: *Impatiens walleriana*
Varietal Denomination: Imtrarose

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/051,269

(22) Filed: Feb. 4, 2005

(65) Prior Publication Data

US 2005/0177916 P1 Aug. 11, 2005

(30) Foreign Application Priority Data

Feb. 6, 2004 (GB) ..... 0402658

(51) Int. Cl.
*A01H 5/00* (2006.01)

(52) U.S. Cl. ..... Plt./317

(58) Field of Classification Search ..... Plt./317
See application file for complete search history.

*Primary Examiner*—Anne Marie Grunberg
*Assistant Examiner*—Georgia Helmer
(74) *Attorney, Agent, or Firm*—Bruce Vrana

(57) ABSTRACT

A new and distinct variety of *Impatiens* plant particularly distinguished by its flat and strong outward spreading growth habit, freely branching with branches that tend to grow horizontally, resulting in a big and floriferous plant with large rose flowers.

1 Drawing Sheet

Latin name of the genus and species of the plant claimed: *Impatiens walleriana.*
Varietal denomination: 'Impatiens'.

BACKGROUND OF THE NEW PLANT

The present invention comprises a new distinct cultivar of *Impatiens*, botanically known as *Impatiens walleriana.*

The new *Impatiens* is a product of a planned breeding program conducted in Enkhuizen, Netherlands. The objective of the breeding program was to develop new *Impatiens* cultivar in a flat and spreading growing type, floriferous with large flowers and with attractive foliage.

The present cultivar originated from a cross-pollination made in 1999, of a proprietary *Impatiens* selection identified as 'P2076-2,' not patented, as the female, or seed parent, with a proprietary *Impatiens* selection identified as 'P1291-4' not patented, as the male, or pollen parent.

The present cultivar has been repeatedly asexually reproduced by cuttings in Enkhuizen, Netherlands, in Angers, France and in Gilroy, Calif., United States of America over a four-year period.

This new *Impatiens* plant is an annual in most climatical zones in the USA, only in zones 9 and 10 it is a perennial plant.

DESCRIPTION OF THE DRAWING

This new *Impatiens* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Impatiens*. The data that define these characteristics were collected from asexual reproductions carried out in Enkhuizen, Netherlands. The plant history was taken on 25 week old plants, blossomed under natural light in the field.

Colour readings were taken in the greenhouse under ambient light. Colour references are primarily to The R.H.S. Colour Chart of The Royal Horticultural Society of London.

Plants of the new *Impatiens* differ primarily from the plants of the female parent selection in the following characteristics:

Plants of the new *Impatiens* have rose flowers and a good trailing habit, whereas the plants of the female have orange flowers and an upright habit.

Plants of the new *Impatiens* differ primarily from the male parent selection in the following characteristics:

Plants of the new *Impatiens* have large rose flowers, whereas the plants of the male have medium sized pink flowers.

TABLE 1

Differences between the new cultivar 'Sutcabl', its parents and a similar cultivar

| | 'Sutcabl' | 'B21' | 'B23' | 'Blue Showers' |
|---|---|---|---|---|
| Flower color | Deep Blue | Deep blue | White | Blue |
| Stem thickness | Thick | Medium | Thick | Thin |
| Plant habit | Compact | Trailing | Compact | Trailing |
| Flower size | Medium | Big | Small | Small |

The family relationship between 'Imtrarose' and 'Imtrared' is through the male parent lines. The male parent line of 'Imtrarose' is RBGE 19821569×J475-2 crossed with M1007-1. The male parent line of 'Imtrared' is RBGE 19821569×J475-2 crossed with M1236-1.

The Plant:
Parentage:
*Female parent.*—'P2076-2,' not patented.
*Male parent.*—'P1291-4,' not patented.
Propagation:
*Type cutting.*—Terminal cuttings.
*Time to initiate roots.*—10–12 days at 2 degrees C.
*Time to produce a rooted cutting.*—4 weeks.
*Root description.*—Fine, fibrous and white in colour.
Plant description:
*General appearance.*—Makes long branches that tend to grow horizontally.
Habit:
*Growth and branching habit.*—Freely branching habit, freely flowering, vigorous.
*Plant height.*—20–30 cm.
*Plant spread.*—100 cm.
Lateral branch description:
*Length.*—30–37 cm.
*Diameter.*—3–4 mm.
*Texture.*—Smooth, glabrous.
*Internode length.*—0.5–6 cm.
*Color.*—RHS 146C and 184A.
Foilage description:
*Arrangement.*—Alternate/opposite.
*Length, mature leaves.*—5.8–6.6 cm.
*Width, mature leaves.*—3.4–4 cm.
*Shape.*—Broadly elliptic.
*Apex.*—Acuminate.
*Base.*—Acute.
*Margin.*—Serrate.
*Texture.*—Smooth, glabrous.
*Venation pattern.*—Pinnate.
*Color young foliage, upper surface.*—RHS 146B.
*Color young foliage, lower surface.*—RHS 147C and 182B.
*Fully expanded foliage, upper surface.*—RHS 146A.
*Fully expanded foliage, lower surface.*—RHS 146B.
*Venation, upper surface.*—RHS 146C.
*Venation, lower surface.*—RHS 146B.
*Petiole length.*—About 1.7–2.5 cm.
*Petiole diameter.*—About 2 mm.
*Texture.*—Smooth, glabrous.
*Color.*—RHS 145B.
Flower description:
*Flower type and flowering habit.*—Single.
*Number of flowers per leaf axil.*—2.
*Number of flowers and flower buds per lateral branch.*—15–23.
*Flower position.*—Above and beyond the foliage and typically facing upwards and outward.
*Flower shape.*—Rounded, mostly flat.
*Flowers lasting.*—About 7–9 days on the plant depending on environmental conditions.

Flowers non persistent.
Flowers not fragrant.
Flowering indeterminate and continuous.

*Flowering season.*—Year round under greenhouse conditions. In the garden, flowering from Spring until Fall.
*Flower diameter.*—About 4.5–4.7 cm.
Flower bud:
*Rate of opening.*—From flower bud to fully open flower, typically about 6–8 days depending on temperature.
*Bud length (at stage of showing color).*—About 1.5 cm.
*Bud diameter.*—About 1 cm.
*Bud shape.*—Ovoid.
*Texture.*—Smooth, glabrous.
*Color, just before opening.*—RHS 73A.
Petals:
*Lateral sepals.*—2.
*Shape.*—Linear-lanceolate.
*Apex.*—Acute.
*Margin.*—Entire.
*Length.*—3–7 mm.
*Texture upper surface and lower surface.*—Smooth, glabrous.
Spur:
*Length.*—About 3 cm.
*Texture.*—Smooth, glabrous.
*Aspect.*—Curved.
*Color.*—RHS 172B.
Peduncles:
*Length.*—About 2.3 cm.
*Diameter.*—1 cm.
*Aspect.*—About 45 degrees from the stem.
*Color.*—RHS 146C.
*Bracts.*—At least 2.
*Shape.*—Linear-lanceolate/subulate.
*Apex.*—Acute.
*Length.*—3–6 mm.
*Color.*—RHS 146A.
Reproductive organs:
*Androecium.*—Stamen number: Five fused at anthers, filaments free, hooded.
*Anther shape.*—Obovate.
*Anther length.*—About 4 mm.
*Anther color.*—RHS 67A.
*Amount of pollen.*—No pollen.
Gynoecium:
*Pistil number.*—One.
*Pistil length.*—About 4 mm.
*Stigma shape.*—Columnar, five segmented.
*Stigma color.*—Red purple.
*Style color.*—RHS 67A.
*Ovary arrangement.*—Five celled.
*Ovary color.*—RHS 146A.
*Seed development.*—Seed development has not been observed.
*Disease tolerance to date.*—No known susceptibility to diseases or insects noted.

What is claimed is:

1. A new and dstinct variety of *Impatiens* plant named 'Imtrarose', substantially as illustrated and described herein.

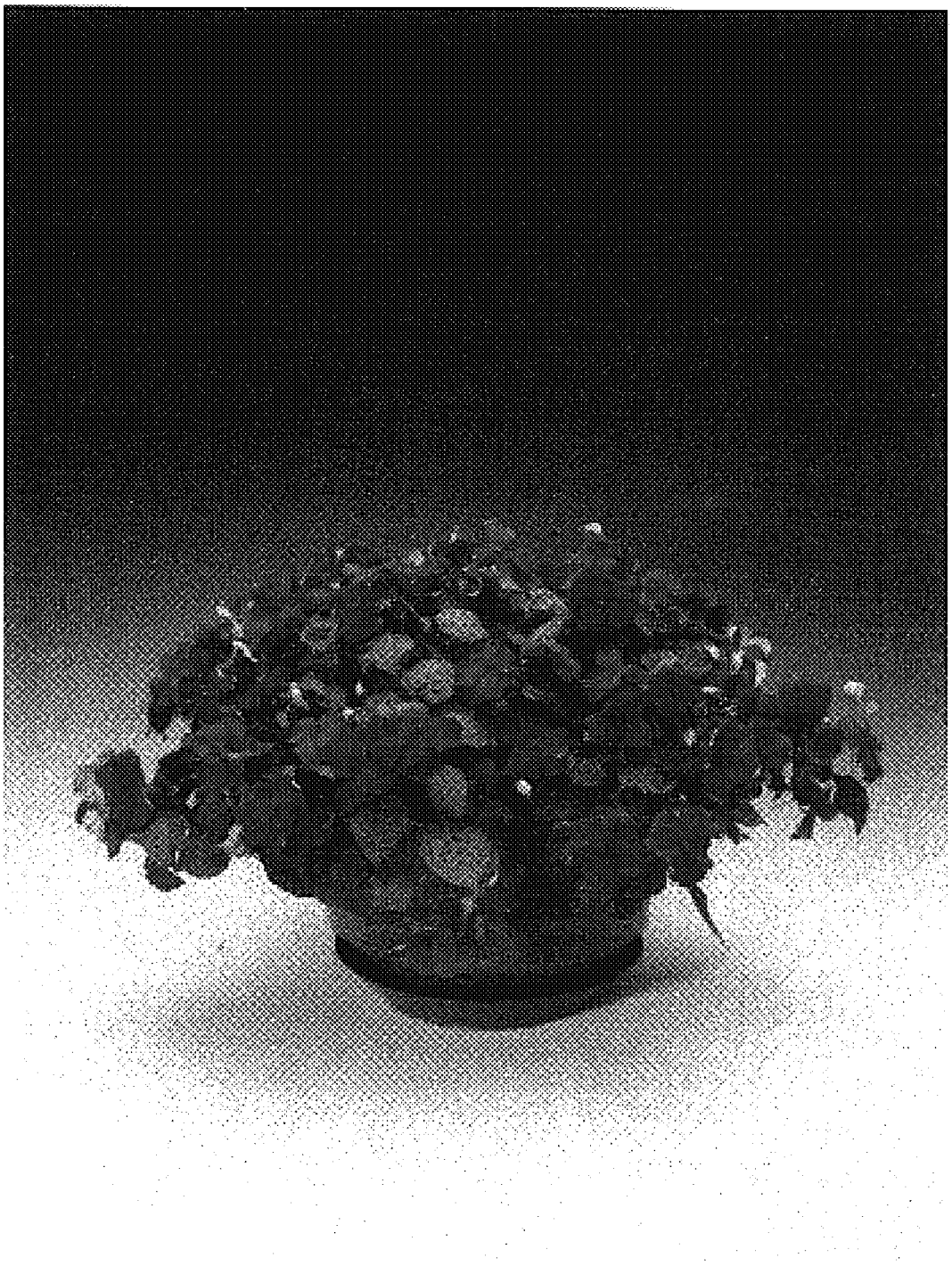

* * * * *